United States Patent [19]

Descamps et al.

[11] Patent Number: 4,977,274
[45] Date of Patent: Dec. 11, 1990

[54] 4-HYDROXYINDOLE DERIVATIVES, THE PROCESS FOR PREPARATION THEREOF AND THEIR USE

[75] Inventors: Marcel Descamps, Wavre; Walter Verstraeten, Mechelen, both of Belgium

[73] Assignee: Sanofi, Paris, France

[21] Appl. No.: 398,922

[22] Filed: Aug. 28, 1989

Related U.S. Application Data

[63] Continuation of Ser. No. 923,217, Oct. 27, 1986, abandoned.

[30] Foreign Application Priority Data

Nov. 12, 1986 [FR] France ................ 85 16676

[51] Int. Cl.$^5$ .................................... C07D 403/12
[52] U.S. Cl. .................... 548/455; 548/467; 548/483; 548/486; 548/501; 548/502; 548/509
[58] Field of Search ............ 548/455, 509, 501, 502, 548/503, 486, 483, 467

[56] References Cited

U.S. PATENT DOCUMENTS 3,471,515 10/1969 Troxler et al. ............... 548/503
4,287,125 9/1981 Soula ....................... 568/39
4,510,315 4/1985 Demarne et al. ............. 548/455

FOREIGN PATENT DOCUMENTS 0005828 12/1979 European Pat. Off. .
002511  7/1980 European Pat. Off. .
0013878  8/1980 European Pat. Off. .
57-142969 of 1982 Japan .

OTHER PUBLICATIONS

Helv. Chimica Acta, vol. 54, p. 2411 (1971) Seemann et al., Beitrage zur Chemie der 4–Hydroxyindol-Verbindungen.
W. Weber et al., Phase Transfer Catalysis in Organic Synthesis, Springer-Verlag, New York (1977), pp. 1-9.
W. Houlihan, Indoles Part Three, p. 171, John Wiley and Sons, Inc. N.Y. (1979).

Primary Examiner—Mary E. Ceperley
Attorney, Agent, or Firm—Bacon & Thomas

[57] ABSTRACT

The invention relates to new 4-hydroxyindole derivatives of general formula:

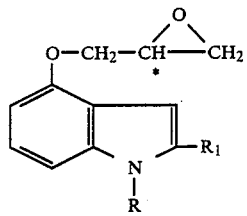

in which R represents a labile protective group and $R_1$ can represent hydrogen, a $C_1$–$C_6$ alkyl radical, a $C_3$–$C_6$ cycloalkyl radical, a lower alkoxy radical, a lower hydroxyalkyl radical, a lower (lower alkoxy) alkyl radical, a phenyl radical optionally substituted with a halogen atom or a lower alkyl or lower alkoxy radical, a cyano radical, a radical of formula

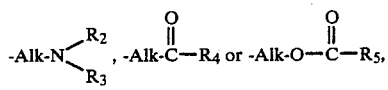

in which $R_2$ and $R_3$, which may be identical or different, each represent hydrogen or a lower alkyl radical, $R_4$ represents a hydroxy group, a lower alkyl or lower alkoxy radical or a radical

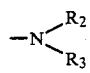

in which $R_2$ and $R_3$ have the same meaning as above, $R_5$ represents a lower alkyl radical and Alk represents a single bond or a straight- or branched-chain alkylene radical having from 1 to 4 carbon atoms.

The invention also relates to a process for preparing 4-(3-amino-2-hydroxypropoxy)indole derivatives from the said 4-hydroxyindole derivatives.

8 Claims, No Drawings

4-HYDROXYINDOLE DERIVATIVES, THE PROCESS FOR PREPARATION THEREOF AND THEIR USE

This application is a continuation of application Ser. No. 06/923,217, filed Oct. 27, 1986 now abandoned.

The present invention relates to 4-hydroxyindole derivatives, the process for preparation thereof and their use.

The 4-hydroxyindole derivatives of the invention can be represented by the general formula:

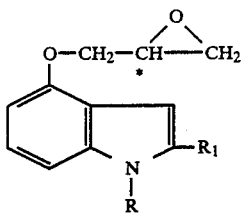

in which R represents a labile protective group and $R_1$ can represents :
 hydrogen,
 a straight- or branched-chain alkyl radical having from 1 to 6 carbon atoms,
 a cycloalkyl radical having from 3 to 6 carbon atoms,
 a lower alkoxy radical,
 a lower hydroxyalkyl radical,
 a lower lower (lower alkoxy)alkyl radical,
 a phenyl radical optionally substituted with a halogen atom or with a lower alkyl or lower alkoxy radical,
 a cyano radical,
 a radical of formula:

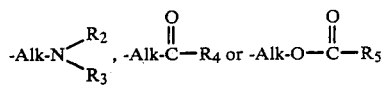

in which:
 $R_2$ and $R_3$, which may be identical or different, each represent hydrogen or a loweralkyl radical,
 $R_4$ represents a hydroxy group, a lower alkyl or lower alkoxy radical or a radical

in which $R_2$ and $R_5$ have the same meaning as above,
 $R_5$ represents a lower alkyl radical, and
Alk represents a single bond or straight- or branched-chain alkylene radical having from 1 to 4 carbon atoms.

In the present context, the terms listed below imply the following meaning :
 "Labile protective group" denotes a readily removable protective group such as, by way of example, an alkylcarbonyl group such as formyl, acetyl or propionyl, an arylcarbonyl group such as benzoyl, an alkylsulphonyl group such as methanesulphonyl or an arylsulphonyl group such as benzenesulphonyl or p-toluenesulphonyl, the arylsulphonyl group, more particularly the benzenesulphonyl and p-toluenesulphonyl groups constituting preferred groups ;
 "Lower alkyl" denotes straight or branched saturated aliphatic hydrocarbon residues containing up to four carbon atoms, such as methyl, ethyl, n-propyl, isopropyl, n-butyl, isobutyl or tert-butyl ;
 "Lower alkoxy" denotes a hydroxy group substituted with a lower alkyl radical as defined above.

Thus, taking into account the meanings given above, $R_1$ can represent, in particular, hydrogen or a methyl, ethyl, n-propyl, isopropyl, n-butyl, isobutyl, tert-butyl, 1-methylpropyl, n-pentyl, n-hexyl, cyclohexyl, methoxy, ethoxy, hydroxymethyl, 1-hydroxyethyl , methyloxymethyl, phenyl, chlorophenyl, methylphenhyl, methoxyphenyl, cyano, methylamino, dimethylamino, methylamino- or ethylaminoethyl, dimethylamino- or diethylaminoethyl, carboxy, methoxycarbonyl, ethoxycarbonyl, (2-methyl-2-methoxycarbonyl)-propyl, carbamoyl, N,N-dimethyl- or N,N-diethylcarbamoyl, acetylk, propionyl, acetoxyumethyl or pivaloyloxymethyl radical.

However, hydrogen and methyl are preferred values of $R_1$.

As a result of the asymmetric carbon atom, represented by an asterisk, the compounds of formula I can take the form of laevorotaory or dextrorotatory isomers, or mixtures of these isomers.

The invention hence relates to the 4-hydroxy-indole derivatives in the form of separate laevorotatory and dextrorotatory isomers, or in the form of mixtures of these isomers such as in the form of the racemic mixture.

The compounds of the invention were found to be especially useful as intermediate products, in particular for preparing 4-(3-amino-2-hydroxypropoxy)indole derivatives of general formula :

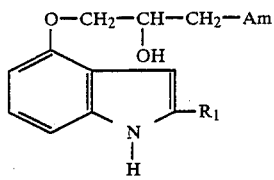

in which $R_1$ has the same meaning as above and Am represents a substituted or unsubstituted amino radical, and their salts.

Such products are described, in particular, in U.S. Pat. Nos. 3,471,515 and 4,076,829 and French Patent No. 8067 M, and in European Patent Application No. 25,727.

These compounds are of undeniable value on account of their β-adreno-receptor-blocking properties, which make them useful in the cardiovascular field.

Another subject of the invention consequently relates to the 4-hydroxyindole derivatives of formula I as new industrial products which are useful, in particular, as intermediates, for example for the final synthesis of the 4-(3-amino-2-hydroxypropoxy)indole derivatives of formula Ia.

A process has been described in U.S. Pat. No. 3,471,515 and French Patent No. 1,598,040, for the preparation of 4-(3-amino-2-hydroxypropoxy)indole derivatives by reaction of 4-hydroxyindole with epichlorohydrin or epibromohydrin, in racemic form or laevorotatory form, in alkaline medium and in the absence of oxygen, followed by condensation of the compounds obtained with an amine.

In connection with the development of the present invention, an attempt was made to prepare 4-(3-amino-2-hydroxypropoxy)indole derivatives of formula Ia according to the method described above as given in the prior art, namely without isolating the compounds formed after reaction of 4-hydroxyindole with epichlorohydrin.

This method, however, only gave poor yields of the 4-(3-amino-2-hydroxypropoxy)indole derivative in question.

For example, it was not possible to obtain more than 20 to 25% of 4-{3-[2-(1H-indol-3-yl)-1,1-dimethylethylamino]-2-hydroxypropoxy} indole of formula Ia by condensation of 4-hydroxyindole with dimethyltryptamine.

On the other hand, it is known that, by reacting 4-hydroxyindole with epichlorohydrin, a mixture of compounds consisting, in particular, of 4-oxiranylmethoxyindole and, in a smaller proportion, 4-(3-chloro-2-hydroxypropoxy)indole is obtained.

In consequence, 4-{3-[2-(1H-indol-3-yl)-12,1-dimethylethylmaino]-2-hydroxypropoxy}indole was also prepared by condensation of dimethyltryptamine with 4-oxiranylmethoxyindole isolated and purified from its reaction medium (Helv. Chinica Acta, Vol. 54, p. 2411, (1971).

Although the yields of 4-(2-hydroxypropoxy) indole derivative so produced are higher than those obtained without intermediate purification of the 4-oxiranylmethoxyindole, this method of carrying out the reaction nevertheless has several disadvantages, such as to make the process workable only with difficulty on a large scale.

In effect, since 4-oxiranylnusthoxyindole is a compound having a poorly defined melting point (between 50° and 60° C.), it cannot be purified by crystallization but requires the use of a method which is much more difficult to extrapolate to the industrial level, such as column chromatography.

In addition, 4-oxiranylmethoxyindole is a very light-sensitive product, which will cause problems in relation to its storage.

In consequence, the credibility from the industrial standpoint of a process such as that described above appears to be seriously impaired in the light of the results and the disadvantages encountered.

It has now been found, according to the invention, that using a the 4-hydroxyindole derivatives of formula I above enable the 4-(3-amino-2-hydroxypropoxy)indole derivatives of formula Ia to be obtained in overall yields far superior to those obtained according to the prior art, while avoiding the disadvantages of the latter.

The compounds of the invention present in fact an undeniable advantage compared with 4-oxiranylmethoxyindole: they can be used in crude form for the preparation of the compounds of formula Ia in high yields.

Therefore, the isolation and purification of the compounds of the invention can be avoided contrary to 4-oxiranylmethoxyindole which must be isolated and purified for obtaining significant yields in compound of formula Ia.

The compounds of the invention were found, in fact, to be more stable than 4-oxiranylmethoxyindole. Furthermore, the melting point of the compounds of the invention was also found to be more accurate than that of 4-oxiranylmethoxyindole.

Consequently, the compounds of formula I can be isolated, if necessary, according to techniques which are industrially applicable for instance by crystallization and their important stability to light will be useful when storing is required.

Among the 4-(3-amino-2-hydroxypropoxy)indole derivatives of formula Ia above, 4-(3-isopropylamino-2-hydroxypropoxy)indole or pindolol and 4-(3-isopropylamino-2-hydroxypropoxy)-2-methylindole or mepindolol constitute especially advantageous pharmaceutical compounds, and the same applies to another similar derivative, namely, 4-(3-tert-butylamino-2-benzoyloxypropoxy)-2-methylindole or bopindolol.

Therefore, the compounds of formula I which are capable of giving access to these pharmaceutical compounds will constitute preferred derivatives according to the invention, that is to say the compounds of formula I in which R has one of the given meanings, for example arylsulphonyl preferably benzenesulphonyl or p-toluenesulphonyl, and $R_1$ represents hydrogen or a methyl radical.

Thus, the 4-hydroxyindole derivatives of formula Ia and their salts can be obtained in accordance with the invention, by treating, under reflux, a compound of formula I above with an amine of general formula:

$$H—AM \qquad II$$

in which Am represents a substituted or unsubstituted amino group, for example isopropylamino, tert-butylamino or 2-(1H-indol-3-yl)-1,1-dimethylethylamino, this being performed in a suitable solvent, such as a lower alcohol for example ethanol, n-propanol or isopropanol, or such as an excess of amine of formula II, so as to form a 4-(2-hydroxypropoxy)indole derivative of general formula:

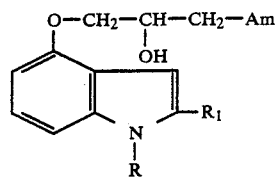

in which R, $R_1$ and Am have the same meaning as above, which derivative is deprotected, in a traditional manner, for example by heating under reflux in a suitable solvent such as a lower alcohol, for example ethanol, n-propanol or isopropanol, and in the presence of an alkali metal hydroxide such as sodium hydroxide, which provides the desired compound of formula Ia which, if desired, is reacted with an acid to form a salt thereof.

In general, the compound of formula III is isolated from its preparation medium in the form of an addition salt, for example in the form of hydrochloride.

This method enables 4-(3-amino-2-hydroxypropoxy)indole derivatives of formula Ia to be obtained in good yield, the latter being as high as 75% in some cases, from the compound of formula I.

With regard to the 4-hydroxyindole derivatives of the invention, these can be obtained by reacting an N-protected indole derivative of general formula:

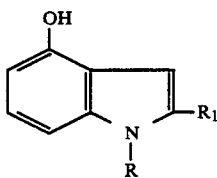

in which R and R₁ have the same meaning as above, with epichlorohydrin or epibromohydrin in the presence of a metalating agent and optionally in the presence of a phase transfer catalyst.

As a metalating agent, any basic compound capable of salifying the 4-hydroxy group of the derivative of formula IV may be envisaged, for example an alkali metal hydride such as sodium or potassium hydride, an alkali metal hydroxide such as sodium or potassium hydroxide, an alkali metal carbonate, for example sodium or potassium carbonate, or an alkali metal alcoholate such as sodium methanolate.

The reaction takes place at the refluxing temperature and in a suitable single-phase medium, generally an aromatic hydrocarbon such as toluene or a lower alcohol such as methanol, or alternatively in a two-phase medium such as a water/methylene chloride mixture.

Furthermore, the epichlorohydrin or epibromohydrin used will be in the form of dextrorotatory or laevorotatory isomer, or in the form of a mixture of these isomers, for example in the form of a racemate, so as to produce the compounds of formula I, respectively, in the form of the dextrorotatory or laevorotatory isomer or in the form of a mixture of these isomers.

With regard to the phase transfer catalyst, this will be, for example, a tetrabutylammonium salt such as the chloride or hydrogen sulphate, but preferably a tris(dioxaalkyl)amine, such as tris(3,6-dioxaheptyl)amine or TDA-1.

It has, in fact, been observed that the 4-hydroxyindole derivatives of the invention can be obtained in virtually quantitative yields from the N-protected indole derivative of formula IV more particularly from 1-benzenesulphonyl- or 1-(p-toluenesulphonyl)-4-oxiranylmethoxyindole when the reaction is carried out in the presence of a tris(dioxaalkyl) amine, preferably tris(3,6-dioxaheptyl)amine.

High yields in compound of formula Ia can be obtained when the derivative of formula I so provided is used in crude form, such yields being, in some cases, superior to 70% from the N-protected 4-hydroxyindole of formula IV.

Yet, another object of the invention relates to a process for preparing ring 4-(3-amino-2-hydroxypropoxy)indole derivatives of formula Ia above and salts thereof, process which comprises:
  reacting under reflux and in an appropriate medium as described above, a N-protected indole derivative of formula IV with epichlorohydrin or epibromohydrin in the presence of a metalating agent as described above and a tris(dioxaalkyl)amine as phase transfer catalyst to obtain a compound of formula I in crude form,
  treating under reflux the crude compound of formula I so obtained, with an amine of formula II, this being performed in a suitable solvent such as described above, so as to form a 4-(2-hydroxypropoxy) indole derivative of formula III,
  deprotecting the compound of formula III by heating under reflux in a suitable solvent as described above and in the presence of an alkali metal hydroxide, which provides the desired compound of formula Ia which, if desired, is reacted with an acid to form a salt thereof.

The indole derivatives of formula IV are new products, with the exception of 1-(p-toluenesulphonyl)-4-hydroxyindole, which is described in Japanese Patent Application No. 142,968/82 (C.A. 98: 71922 m).

These indole derivatives of formula II can be obtained by treating under reflux a tetrahydroindole derivative of general formula:

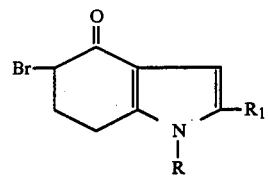

in which R and R₁ have the same meaning as above, with a tertiary amine such as triethylamine, in a suitable solvent such as a non-polar solvent, for example toluene.

As regards the compounds of formula V, these can be prepared according to the method described in U.S. Pat. No. 3,654,303.

The following non-limiting Examples illustrate the invention :

EXAMPLE 1

Preparation of 1-(p-toluenesulphonyl)-4-oxiranylmethoxyindole

Into a 500-ml flask equipped with a condenser and a nitrogen inlet were introduced 32.6 g (0.113 mol) of 1-(p-toluenesulphonyl)-4-hydroxyindole, 230 ml of methanol, 20 g (0.144 mol) of potassium carbonate and 30.7 g (0.331 mol) of epichlorohydrin.

The mixture was heated to reflux for 4 h under nitrogen atmosphere and then brought to dryness under vacuum. Approximately 100 ml of methylene chloride and approximately 10 ml of water were added and the mixture was then extracted twice with methylene chloride. The organic phase was washed with water, then three times with 5% strength sodium hydroxide, and finally three times with water. The mixture was dried, decolorized and filtered. It was brought to dryness under vacuum, a little ethyl ether was added, and the mixture was placed in a refrigerator to induce the precipitation of the desired compound which was then filtered.

In this manner, 17.5 g of 1-(p-toluenesulphonyl)-4-oxiranylmethoxyindole were obtained, which represents a 45.1% yield.

M.P.: 116°–119° C.

EXAMPLE 2

Preparation of 1-(p-toluenesulphonyl)-4-oxiranylmethoxyindole

Into a 250-ml flask were introduced 2.87 g (0.01 mol) of 1-(p-toluenesulphonyl)-4-hydroxyindole, 0.34 g of tetrabutylammonium hydrogen sulphate and 45 ml of methylene chloride. The mixture was stirred for five minutes and 10 ml of a 50% strength aqueous sodium hydroxide solution then added. The mixture was stirred again for five minutes and 1.18 ml (0.015 mol) of epichlorohydrin was introduced.

During the addition of sodium hydroxide, a precipitate appeared. The mixture was stirred for three hours and 20 ml of water were then added to bring about solubilization of the precipitate. The mixture was stirred again for 3 h and heated under reflux for about six hours. Then 1 ml of epichlorohydrin was added and the mixture was heated under reflux for three hours. The mixture was decanted and the organic phase washed with water and dried. It was filtered and brought to dryness under vacuum until a pasty residue was obtained. Ethyl ether was added and the mixture was filtered. The filtrate was brought to dryness under vacuum, a little ethyl ether was added and the mixture was maintained in the refrigerator to induce the precipitation of the desired compound which was then filtered.

In this manner, 1 g of 1-(p-toluenesulphonyl)-4-oxiranylmethoxyindole was obtained, which represents a 29% yield.

EXAMPLE 3

Preparation of
1-benzenesulphonyl-4-oxiranylmethoxyindole

Into a 100 ml flask fitted with a thermometer, a condenser and a stirrer were introduced 2.5 g (0.09 mol) of 1-benzenesulphonyl-4-hydroxyindole, 20 ml of methanol, 1.53 g of potassium carbonate and 2 ml of epichlorohydrin. The mixture was stirred for 5 min. and heated to 90° C. (water bath) for 30 min. The solution was poured into water and the mixture extracted twice with methylene chloride. The organic phase was washed with dilute aqueous potassium hydroxide solution, and then twice with water. The mixture was dried and evaporated to dryness, and the desired compound was crystallized in isopropanol.

In this manner, 1-benzenesulphonyl-4-oxiranylmethoxyindole was obtained in a 33% yield.
M.P.: 96° C.

EXAMPLE 4

Preparation of
4-(3-isopropylamino-2-hydroxypropoxy)indole or pindolol (a) 1-(p-Toluenesulphonyl)-4-oxiranylmethoxyindole.

In a flask 350 g (1.232 mol) of 1-(p-toluenesulphonyl)-4-hydroxyindole were brought to reflux in 1 l of toluene so as to remove the water. After the mixture was cooled, 54 g (1.35 mol) of 55% strength sodium hydride were added. The mixture was heated to reflux and taken to dryness under vacuum. After this operation, 1,302 g (14 mols) of epichlorohydrin and 19.7 ml (0.06 mol) of tris(3,6-dioxaheptyl)amine were introduced. The mixture was brought to 100° C. for 4 h under a stream of nitrogen and brought to dryness under vacuum. After that, 1,000 ml of methylene chloride and about 100 ml of water were then added. The mixture was washed twice with water, and the solvents were dried over anhydrous sodium sulphate, decolorized and filtered.

In this manner, about 420 g of crude 1-(p-toluenesulphonyl)-4-oxiranylmethoxyindole was obtained, which represents a 100% yield.
Purity: 95.79%
M.P.: 109°–112° C.

Using the same process as that described above, 1-benzenesulphonyl-4-oxiranylmethoxyindole was prepared in an approximately 100% yield.
Purity: 94.6%.

(b)
1-(p-Toluenesulphonyl)-4-(3-isopropyelamino-2-hydroxypropoxy)indole hydrochloride Into a Parr-flask were introduced 17 g (0.05 mol) of 1-(p-toluenesulphonyl)-4-oxiranylmethoxyindole, as previously obtained and 250 ml of isopropylamine and the mixture was then heated to 100° C. After 48 h, the reaction was complete. The medium was evaporated to dryness under vacuum and the hydrochloride precipitated by adding a solution of hydrogen chloride in ethyl acetate. The mixture was stirred for one hour and filtered, and the product washed with ethyl acetate.

In this manner, 12 g of 1-(p-toluenesulphonyl)-4-(3-isopropylamino-2-hydroxypropoxy)indole hydrochloride were obtained after 2 recrystallizations from ethanol.
Yield: 54.6%
MP.: 223°–224° C.
NMR, IR spectra: correct

| Analysis: | C % | H % | N % |
|---|---|---|---|
| Calculated | 57.46 | 6.20 | 6.38 |
| Found | 57.10 | 6.36 | 6.12 |

(c) 4-(3-Isopropylamino-2-hydroxypropoxy)indole

Into a flask equipped with a condenser were introduced 10 g (0.027 mol) of 1-(p-toluenesulphony)-4-(3-isopropylamino-2-hydroxypropoxy)indole hydrochloride, 60 ml of ethanol and 4 g (0.1 mol) of sodium hydroxide in 22 ml of water. The mixture was heated under reflux for 4 h under nitrogen, and left to stand for 12 h. The desired product crystallized. It was filtered off and recrystallized from isopropanol.

In this manner, 4.5 g of 4-(3-isopropylamino-2-hydroxypropoxy)indole were obtained.
Yield: 69.6%
M.P.: 162° C.
Purity: 100%

| Analysis | C % | H % | N % |
|---|---|---|---|
| Calculated | 67.71 | 8.12 | 11.28 |
| Found | 67.93 | 8.21 | 11.47 |

EXAMPLE 5

Preparation of
4-{3-[2-(1H-indol-3-yl)-1,1-dimethylethylamino]-2-hydroxypropoxy{indole hydrochloride (a)
1-(p-Toluenesulphonyl)-4-{3-[2-(1H-indol-3-yl)-1,1-dimethylethylmaino]-2-hydroxypropoxy}-indole hydrochloride Into a 3-1 flask were introduced 172 g (0.5 mol) of 1-(p-toluenesulphonyl)-4-oxiranylmethoxyindole as obtained in Example 4a, 94.13 g (2 mols) of dimethyltryptamine and 21 g of isopropanol.

Under nitrogen atmosphere, the mixture was heated under reflux for 12 hours and then brought to dryness. The residue was taken up in 4 l of ethyl acetate and a solution of gaseous hydrogen chloride in ethyl acetate was added. The mixture was stirred for 2 h, filtered and washed with ethyl acetate.

In this manner, 220 g of 1-(p-toluenesulphonyl)-4-{3-[2-(1H-indol-3-yl)-1,1-dimethylethylamino]-2-hydroxypropoxy}indole hydrochloride were obtained.

Yield: 77.5%
Purity: 94.54%
NMR, IR spectra: in agreement

| Analysis: | C % | H % | N % | S % | Cl % |
|---|---|---|---|---|---|
| Calculated | 63.42 | 6.03 | 7.40 | 5.64 | 6.24 |
| Found | 63.77 | 5.94 | 7.32 | 5.67 | 6.34 |

4-{3-[2-1H-Indol-3-yl)-1,1-dimethylethylamino]-2-hydroxypropoxy}indole hydrochloride Into a 3-1 flask were introduced 200 g (0.352 mol) of 1-(p-toluenesulphonyl)-4-{3-[2-(1H-indol-3-yl)-1,1-dimethylethylamino[-2-hydroxypropoxy}indole hydrochloride, 900 ml of ethanol and 61 g (0.655 sodium hydroxide in 325 ml of water. The mixture was heated under reflux for 4 h under a nitrogen atmosphere and then poured into 14 l of water. The mixture was stirred for 1 h, washed and dried, to obtain 130 g of 4-{3-[2-(1H-indol-3-yl)-1,1-dimethylethylamino]-2-hydroxypropoxy}indole in the form of the base.

Yield: 100%
Purity: 95.77%

The base obtained was dissolved in isopropanol and the insoluble material filtered off. A solution of hydrogen chloride in isopropanol was added to the solution obtained, thereby inducing, on stirring, the precipitation of the hydrochloride after a few hours. The product was filtered off and washed with isopropanol.

In this manner, 4-{3-[2-(1H-indol-3-yl)-1,1-dimethylethylamino]-2-hydroxypropoxy}indole hydrochloride was obtained.

M.P.: 95°–113° C.

We claim:

1. A process for preparing 4-(3-amino-2-hydroxypropoxy)indole derivatives having a formula:

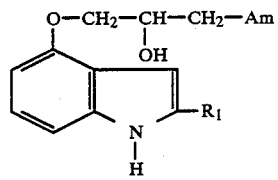

in which $R_1$ can represent a hydrogen atom; a straight- or branched-chain alkyl group having from 1 to 6 carbon atoms; a cycloalkyl group having from 3 to 6 carbon atoms; a lower alkoxy group; a lower hydroxyalkyl group; a lower (lower alkoxy) alkyl group; a phenyl group optionally substituted with a halogen atom or with a lower alkyl or lower alkoxy group; a cyano group; a group of formula:

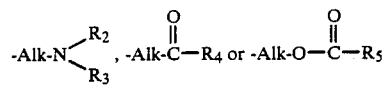

in which:

$R_2$ and $R_3$, which may be identical or different, each represent hydrogen or a lower alkyl group;

$R_4$ represents a hydroxy group, a lower alkyl or lower alkoxy group or a

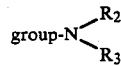

in which $R_2$ and $R_3$ have the same meaning as above, $R_5$ represents a lower alkyl group; and Alk represents a single bond or a straight- or branched-chain alkylene group having from 1 to 4 carbon atoms;

and Am represents a substituted or unsubstituted amino group, and salts thereof, wherein a 4-hydroxyindole derivative having a formula

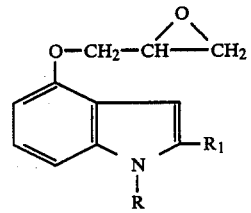

in which R represents a labile protective group and $R_1$ is as defined above, is reacted with an amine having a formula H-Am, where Am is as defined above, in an excess of said amine or in a lower alcohol to form a 4-(2-hydroxypropoxy)indole derivative of formula:

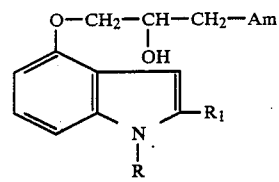

in which R, $R_1$ and Am have the same meaning as above, which derivative is deprotected by heating under reflux in a lower alcohol and in the presence of an alkali metal hydroxide to obtain the desired 4-(3-amino-2-hydroxypropoxy)indole derivative which is optionally further reacted with an acid to form a salt thereof.

2. A process for preparing a 4-(3-amino-2-hydroxypropoxy)indole having a formula:

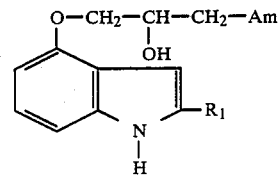

in which $R_1$ can represent a hydrogen atom, a straight, or branched-chain alkyl group having from 1 to 6 carbon atoms, a cycloalkyl group having from 3 to 6 carbon atoms, a lower alkoxy group, a lower hydroxyalkyl group, a lower (lower alkoxy)alkyl group, a phenyl group optionally substituted with a halogen atom or with a lower alkyl or lower alkoxy group, a cyano group, or a radical of formula:

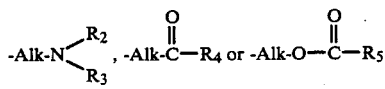

in which:
R₂ and R₃, which may be identical or different, each represent hydrogen or a lower alkyl group;
R₄ represents a hydroxy group, a lower alkyl or lower alkoxy group or a

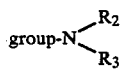

in which R₂ and R₃ have the same meaning as above,
R₅ represents a lower alkyl group; and
Alk represents a single bond or a straight- or branched-chain alkylene group having from 1 to 4 carbon atoms;
and wherein Am represents a substituted or unsubstituted amino group or a salt thereof, wherein a N-protected indole derivative of formula:

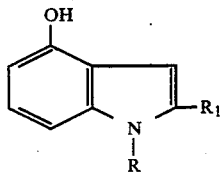

in which R and R₁ have the above meanings, is reacted under reflux and in an appropriate medium, with epichlorohydrin or epibromohydrin in the presence of a metalating agent and a tris (dioxaalkyl) amine as phase transfer catalyst to obtain a 4-hydroxyindole derivative, in crude form; the crude 4-hydroxyindole derivative so obtained is treated with an amine of general formula:

H—Am in which Am has the same meaning as above, in a lower alcohol or an excess of the above amine, so as to form a 4-(2-hydroxypropoxy)indole derivative of general formula:

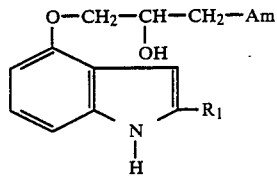

in which R and R₁ have the same meaning as above and Am has the same meaning as above; the 4-(2-hydroxypropoxy)indole derivative so obtained is deprotected by heating under reflux in a lower alcohol and in the presence of an alkali metal hydroxide to obtain the desired 4-(3-amino-2-hydroxypropoxy) indole derivative, which is optionally further reacted with an acid to form a salt thereof.

3. A process according to claim 1 wherein the metalating agent is an alkali metal hydride, an alkali metal hydroxide, an alkali metal carbonate or an alkali metal alcoholate.

4. A process according to claim 1 wherein the medium is a single-phase or two-phase medium.

5. A process according to claim 1 wherein Am represents an isopropyl-amino, tert-butylamino or 2-(1H-indol-3-yl)-1,1-dimethylethylamino group and R₁ represents hydrogen or a methyl group.

6. A process according to claim 2 wherein the metalating agent is an alkali metal hydride, an alkali metal hydroxide, an alkali metal carbonate or an alkali metal alcoholate.

7. A process according to claim 2 wherein the phase transfer catalyst is tris(3,6-dioxaheptyl)amine.

8. A process according to claim 2 wherein Am represents an isopropyl-amino, tert-butylamino or 2-(1H-indol-3-yl)-1,1-dimethylethylamino group and R₁ represents hydrogen or a methyl group.

* * * * *